(12) United States Patent
Elomari

(10) Patent No.: US 6,461,580 B1
(45) Date of Patent: Oct. 8, 2002

(54) USING ZEOLITE SSZ-58 FOR REDUCTION OF OXIDES OF NITROGEN IN A GAS STREAM

(75) Inventor: Saleh Elomari, Richmond, CA (US)

(73) Assignee: Chevron U.S.A. Inc., San Francisco, CA (US)

( * ) Notice: Subject to any disclaimer, the term of this patent is extended or adjusted under 35 U.S.C. 154(b) by 0 days.

(21) Appl. No.: 09/905,350

(22) Filed: Jul. 13, 2001

(51) Int. Cl.⁷ .................................................. C01B 21/20
(52) U.S. Cl. ................................ 423/239.2; 423/213.5; 423/239.2

(58) Field of Search ........................... 423/213.5, 239.2, 423/213.2

(56) References Cited

U.S. PATENT DOCUMENTS 3,832,449 A * 8/1974 Rosinski et al. ........ 208/111.01
5,433,933 A * 7/1995 Eshita et al. ............. 423/213.2

\* cited by examiner

*Primary Examiner*—David Sample
(74) *Attorney, Agent, or Firm*—Richard J. Sheridan

(57) ABSTRACT

The present invention relates to new crystalline zeolite SSZ-58 and processes employing SSZ-58 as a catalyst.

4 Claims, No Drawings a family of crystalline zeolites designated herein "zeolite SSZ-58" or simply "SSZ-58".

USING ZEOLITE SSZ-58 FOR REDUCTION OF OXIDES OF NITROGEN IN A GAS STREAM

BACKGROUND OF THE INVENTION

1. Field of the Invention

The present invention relates to new crystalline zeolite SSZ-58 and processes employing SSZ-58 as a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "zeolite SSZ-58" or simply "SSZ-58". Preferably, SSZ-58 is obtained in its silicate, aluminosilicate, titanosilicate, vanadosilicate or borosilicate form. The term "silicate" refers to a zeolite having a high mole ratio of silicon oxide relative to aluminum oxide, preferably a mole ratio greater than 100, including zeolites comprised entirely of silicon oxide. As used herein, the term "aluminosilicate" refers to a zeolite containing both alumina and silica and the term "borosilicate" refers to a zeolite containing oxides of both boron and silicon.

In accordance with the present invention, there is provided an improved process for the reduction of oxides of nitrogen contained in a gas stream in the presence of oxygen wherein said process comprises contacting the gas stream with a zeolite, the improvement comprising using as the zeolite a zeolite having a mole ratio greater than about 20 of an oxide of a first tetravalent element to an oxide of a second tetravalent element different from said first tetravalent element, trivalent element, pentavalent element or mixture thereof and having, after calcination, the X-ray diffraction lines of Table II. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

DETAILED DESCRIPTION OF THE INVENTION

The present invention comprises a family of crystalline, zeolites designated herein "zeolite SSZ-58" or simply "SSZ-58". SSZ-58 is believed to be a large pore zeolite. As used herein, the term "large pore" means having an average pore size diameter greater than about 6.5 Angstroms, preferably from about 7 Angstroms to about 8 Angstroms.

In preparing SSZ-58 zeolites, a N-butyl-N-cyclooctylpyrrolidinium cation or N-propyl-cyclooctylpyrrolidinium cation is used as a crystallization template. In general, SSZ-58 is prepared by contacting an active source of one or more oxides selected from the group consisting of monovalent element oxides, divalent element oxides, trivalent element oxides, and tetravalent element oxides with the templating agent.

SSZ-58 is prepared from a reaction mixture having the composition shown in Table A below.

TABLE A

| Reaction Mixture | | |
|---|---|---|
| | Typical | Preferred |
| $YO_2/W_aO_b$ | >20 | 35–65 |
| $OH^-/YO_2$ | 0.10–0.50 | 0.15–0.25 |
| $Q/YO_2$ | 0.05–0.50 | 0.10–0.20 |
| $M_{2/n}/YO_2$ | 0.02–0.40 | 0.10–0.30 |
| $H_2O/YO_2$ | 25–100 | 30–50 | wherein Y is silicon, germanium or a mixture thereof; W is aluminum, gallium, iron, boron, titanium, indium, vanadium or mixtures thereof; M is an alkali metal cation, alkaline earth metal cation or mixtures thereof; n is the valence of M (i.e., 1 or 2); Q is a N-butyl-N-cyclooctylpyrrolidinium cation or N-propyl-cyclooctylpyrrolidinium cation., and a is 1 or 2, and b is 2 when a is 1 (i.e., W is tetravalent) and b is 3 when a is 2 (i.e., W is trivalent).

In practice, SSZ-58 is prepared by a process comprising:

(a) preparing an aqueous solution containing sources of at least one oxide capable of forming a crystalline molecular sieve and a N-butyl-N-cyclooctylpyrrolidinium cation or N-propyl-cyclooctylpyrrolidinium cation having an anionic counterion which is not detrimental to the formation of SSZ-58;

(b) maintaining the aqueous solution under conditions sufficient to form crystals of SSZ-58; and (c) recovering the crystals of SSZ-58.

Accordingly, SSZ-58 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a second tetravalent element(s) different from the first tetravalent element(s), trivalent element(s), pentavalent element(s) or mixture thereof. The first tetravalent element(s) is preferably selected from the group consisting of silicon, germanium and combinations thereof. More preferably, the first tetravalent element is silicon. The second tetravalent element (which is different from the first tetravalent element), trivalent element and pentavalent element is preferably selected from the group consisting of aluminum, gallium, iron, boron, titanium, indium, vanadium and combinations thereof. More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides.

Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-58 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the zeolite is prepared using mild stirring or agitation.

During the hydrothermal crystallization step, the SSZ-58 crystals can be allowed to nucleate spontaneously from the reaction mixture. The use of SSZ-58 crystals as seed material can be advantageous in decreasing the time necessary for complete crystallization to occur. In addition, seeding can lead to an increased purity of the product obtained by promoting the nucleation and/or formation of SSZ-58 over any undesired phases. When used as seeds, SSZ-58 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-58 zeolite crystals. The drying step can be performed at atmospheric pressure or under vacuum.

SSZ-58 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 20; and has, after calcination, the X-ray diffraction lines of Table II below. SSZ-58 further has a composition, as synthesized (i.e., prior to removal of the templating agent from the zeolite) and in the anhydrous state, in terms of mole ratios, shown in Table B below.

TABLE B

| As-Synthesized SSZ-58 | |
|---|---|
| $YO_2/W_cO_d$ | >20 |
| $M_{2/n}/YO_2$ | 0.01–0.03 |
| $Q/YO_2$ | 0.02–0.05 | where Y, W, n, M and Q are as defined above and c is 1 or 2; d is 2 when c is 1 (i.e., W is tetravalent) or d is 3 or 5 when c is 2 (i.e., d is 3 when W is trivalent or 5 when W is pentavalent).

SSZ-58 can be made essentially aluminum free, i.e., having a silica to alumina mole ratio of ∞. A method of increasing the mole ratio of silica to alumina is by using standard acid leaching or chelating treatments. However, essentially aluminum-free SSZ-58 can be synthesized directly using essentially aluminum-free silicon sources as the main tetrahedral metal oxide component, if boron is also present. SSZ-58 can also be prepared directly as either an aluminosilicate or a borosilicate.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that SSZ-58 is comprised of a new framework structure or topology which is characterized by its X-ray diffraction pattern. SSZ-58 zeolites, as-synthesized, have a crystalline structure whose X-ray powder diffraction pattern exhibit the characteristic lines shown in Table I and is thereby distinguished from other zeolites.

TABLE I

| As Synthesized SSZ-58 | | |
|---|---|---|
| 2 Theta (deg.)[a] | d | Relative Intensity[b] |
| 7.1 | 12.4 | S |
| 7.7 | 11.5 | M |
| 9.9 | 8.93 | M |
| 10.5 | 8.42 | W |
| 12.1 | 7.31 | M |
| 17.3 | 5.12 | W |
| 19.7 | 4.50 | M |
| 21.0 | 4.23 | S |
| 21.9 | 4.06 | M |
| 22.35 | 3.97 | VS |

[a] ±0.15
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-58 including actual relative intensities.

TABLE IA

| As-Synthesized SSZ-58 | | |
|---|---|---|
| 2 Theta (deg)[a] | d | $I/I_0 \times 100$ |
| 6.90 | 12.80 (Sh) | 6 |
| 7.06 | 12.51 | 39 |
| 7.72 | 1.44 | 16 |
| 9.86 | 8.963 (Sh) | 10 |
| 9.96 | 8.874 | 13 |

TABLE IA-continued

As-Synthesized SSZ-58

| 2 Theta (deg)[a] | d | I/I₀ × 100 |
|---|---|---|
| 10.46 | 8.450 | 10 |
| 12.10 | 7.309 | 18 |
| 14.06 | 6.294 | 9 |
| 14.21 | 6.228 (Sh) | 7 |
| 15.46 | 5.727 | 5 |
| 15.68 | 5.647 | 6 |
| 16.12 | 5.494 | 4 |
| 17.24 | 5.139 | 14 |
| 17.36 | 5.104 (Sh) | 7 |
| 18.76 | 4.726 | 15 |
| 18.92 | 4.687 | 16 |
| 19.72 | 4.498 | 30 |
| 20.22 | 4.388 | 14 |
| 20.70 | 4.288 | 16 |
| 21.00 | 4.227 | 63 |
| 21.16 | 4.195 | 14 |
| 21.26 | 4.176 (Sh) | 12 |
| 21.88 | 4.059 | 26 |
| 22.28 | 3.987 (Sh) | 61 |
| 22.24 | 3.962 | 100 |
| 22.66 | 3.921 | 26 |
| 23.02 | 3.860 | 9 |
| 23.28 | 3.818 | 5 |
| 23.50 | 3.783 | 17 |
| 23.68 | 3.754 | 13 |
| 24.34 | 3.654 | 5 |
| 25.12 | 3.542 | 11 |
| 25.54 | 3.485 | 7 |
| 25.72 | 3.461 (Sh) | 4 |
| 26.12 | 3.409 | 8 |
| 26.58 | 3.351 | 7 |
| 27.30 | 3.264 | 11 |
| 27.58 | 3.232 | 7 |
| 27.94 | 3.191 | 5 |
| 28.50 | 3.129 (Sh) | 8 |
| 28.62 | 3.117 | 11 |
| 29.18 | 3.058 | 2 |
| 29.86 | 2.990 | 5 |
| 30.08 | 2.968 | 5 |
| 30.88 | 2.894 | 3 |
| 31.46 | 2.842 | 2 |
| 31.74 | 2.817 | 4 |
| 32.48 | 2.755 | 1 |
| 32.59 | 2.746 | 2 |
| 32.76 | 2.732 | 3 |
| 33.14 | 2.701 | 4 |
| 33.56 | 2.668 | 3 |
| 33.80 | 2.650 | 2 |
| 34.82 | 2.574 | 2 |
| 35.12 | 2.553 | 1 |
| 35.38 | 2.535 | 3 |
| 35.82 | 2.505 | 6 |
| 36.50 | 2.460 | 6 |
| 37.74 | 2.382 | 4 |
| 37.94 | 2.370 (Sh) | 2 |
| 38.44 | 2.340 | 2 |
| 39.29 | 2.291 | 2 |
| 39.62 | 2.273 | 1 |
| 41.10 | 2.194 | 1 |
| 43.12 | 2.096 | 2 |
| 43.30 | 2.086 | 5 |
| 43.50 | 2.079 | 2 |

[a]±0.15

After calcination, the SSZ-58 zeolites have a crystalline structure whose X-ray powder diffraction pattern include the characteristic lines shown in Table II:

TABLE II

Calcined SSZ-58

| 2 Theta (deg.)[a] | d | Relative Intensity |
|---|---|---|
| 7.1 | 12.4 | VS |
| 7.7 | 11.5 | M |
| 9.9 | 8.93 | M |
| 10.5 | 8.42 | M |
| 12.1 | 7.31 | W |
| 17.3 | 5.12 | W |
| 19.8 | 4.48 | M |
| 21.0 | 4.23 | S |
| 21.9 | 4.06 | M |
| 22.4 | 3.97 | S |

[a]±0.15

Table IIA below shows the X-ray powder diffraction lines for calcined SSZ-58 including actual relative intensities.

TABLE IIA

Calcined SSZ-58

| Two Theta (deg.)[a] | d | I/Io × 100 |
|---|---|---|
| 6.88 | 12.84 (Sh) | 17 |
| 7.06 | 12.51 | 100 |
| 7.70 | 11.47 | 22 |
| 9.86 | 8.963 (Sh) | 20 |
| 9.98 | 8.856 | 35 |
| 10.48 | 8.435 | 15 |
| 12.12 | 7.297 | 9 |
| 14.20 | 6.232 | 11 |
| 15.48 | 5.720 | 6 |
| 15.70 | 5.640 | 10 |
| 15.84 | 5.590 | 7 |
| 16.14 | 5.487 | 6 |
| 17.24 | 5.139 | 11 |
| 17.37 | 5.101 | 4 |
| 18.78 | 4.721 | 7 |
| 18.96 | 4.677 | 14 |
| 19.76 | 4.489 | 23 |
| 20.26 | 4.380 | 8 |
| 20.70 | 4.287 | 13 |
| 21.02 | 4.223 | 40 |
| 21.22 | 4.184 (Sh) | 9 |
| 21.90 | 4.055 | 18 |
| 22.35 | 3.975 (Sh) | 39 |
| 22.46 | 3.955 | 64 |
| 22.70 | 3.914 | 18 |
| 23.04 | 3.857 | 3 |
| 23.28 | 3.818 | 3 |
| 23.54 | 3.776 | 13 |
| 23.74 | 3.745 | 8 |
| 24.38 | 3.648 | 3 |
| 25.16 | 3.537 | 8 |
| 25.60 | 3.477 | 5 |
| 25.78 | 3.453 (Sh) | 4 |
| 26.14 | 3.406 | 5 |
| 26.64 | 3.343 | 6 |
| 27.34 | 3.259 | 6 |
| 27.64 | 3.225 | 6 |
| 27.98 | 3.186 | 4 |
| 28.58 | 3.121 (Sh) | 7 |
| 28.68 | 3.110 | 8 |
| 29.20 | 3.056 | 1 |
| 29.88 | 2.988 | 4 |
| 30.19 | 2.958 | 3 |
| 30.92 | 2.890 | 2 |
| 31.48 | 2.840 | 2 |
| 31.74 | 2.817 | 3 |
| 32.54 | 2.750 | 1 |
| 32.76 | 2.731 | 1 |
| 33.18 | 2.698 | 2 |
| 33.62 | 2.664 | 2 |
| 33.86 | 2.645 | 2 |
| 34.88 | 2.570 | 1 |

TABLE IIA-continued

Calcined SSZ-58

| Two Theta (deg.)(a) | d | I/Io × 100 |
|---|---|---|
| 35.20 | 2.548 | 1 |
| 35.42 | 2.532 | 2 |
| 35.90 | 2.499 | 5 |
| 36.54 | 2.457 | 4 |
| 37.80 | 2.378 | 3 |
| 38.00 | 2.366 (Sh) | 2 |
| 38.50 | 2.336 | 1 |
| 39.30 | 2.291 | 1 |
| 43.20 | 2.092 | 2 |
| 43.42 | 2.082 | 4 |
| 43.53 | 2.077 | 3 |

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.20 degrees.

The X-ray diffraction pattern of Table I is representative of "as-synthesized" or "as-made" SSZ-58 zeolites. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-58 are shown in Table II. Calcination can also result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-58 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-58. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-58, the spatial arrangement of the atoms which form the basic crystal lattice of the zeolite remains essentially unchanged.

SSZ-58 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

SSZ-58 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

SSZ-58 may be used for the catalytic reduction of the oxides of nitrogen in a gas stream. Typically, the gas stream also contains oxygen, often a stoichiometric excess thereof. Also, the SSZ-58 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a zeolite is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

EXAMPLES

The following examples demonstrate but do not limit the present invention. The templating agent indicated Table C below is used in these examples.

TABLE C

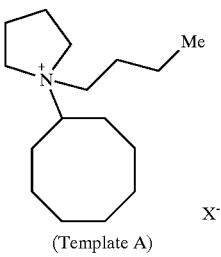
(Template A)

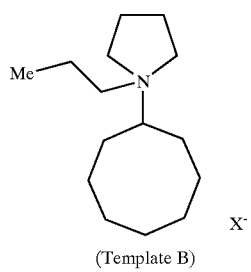
(Template B)

The anion ($X^-$) associated with the cation may be any anion which is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

Example 1

Synthesis of N-butyl-N-cyclooctylpyrrolidinium hydroxide (Template A) I. Synthesis of N-cyclooctylpyrrolidine A three-neck 3000 ml. flask was charged with 75 gm. (1.05 moles) of pyrrolidine, 51 gm. cyclooctanone (0.4 mole) and 80 ml. anhydrous hexane. To the resulting solution, 80 gm. (0.8 mole) of anhydrous magnesium sulfate was added and the mixture was mechanically stirred and heated at reflux (the reaction was monitored by NMR analysis) for 108 hours. The reaction mixture was filtered through a fritted glass funnel. The filtrate was concentrated at reduced pressure on a rotary evaporator to give 70.5 gm. of a clear (yellow-tinted) oily substance. $^1$H-NMR and $^{13}$C-NMR spectra were acceptable for the desired product, 1-(1-pyrrolino)cyclooctene. Saturation of the 1-(1-pyrrolino)cyclooctene to give N-cyclooctylpyrrolidine was accomplished in 98% yield by catalytic hydrogenation in ethanol at a 55 psi pressure of hydrogen gas in the presence of 10% Pd on activated carbon.

II. Quaternization (synthesis of N-butyl-N-cyclooctylpyrrolidinium iodide)

To a solution of 60 gms. (0.33 mole) of N-cyclooctyl pyrrolidine in 600 ml. anhydrous methanol, 150 gm. (0.825 mole) of butyl iodide was added. The reaction mixture was refluxed while stirring for four days. Then an additional equivalent of butyl iodide and one equivalent (33 gm., 0.33 mole) of potassium bicarbonate were added and the mixture was stirred at refluxing temperature for an additional 36 hours. The reaction mixture was concentrated at reduced pressure on a rotary evaporator to give an off-white colored solid material. The solids were rinsed several times with chloroform and filtered after each rinse. All the chloroform rinses were combined and concentrated to give a white powder whose NMR data were acceptable for the desired quaternary ammonium iodide salt. The reaction afforded 109 gm. (90% yield) of N-butyl-N-cyclooctylpyrrolidinium iodide. The iodide salt was purified by recrystallization by completely dissolving the iodide salt in acetone, and then precipitating by the addition of ethyl ether to the acetone solution. This procedure gave 98 gms. of white powder with very clean $^1$H and $^{13}$C-NRM spectra.

III. Ion Exchange (synthesis of N-butyl-N-cyclooctylpyrrolidinium hydroxide)

N-butyl-N-cyclooctylpyrrolidinium iodide salt (95 gms., 0.26 mole) was dissolved in 300 ml. water in a 1000 ml. plastic bottle. To the solution, 300 gms. of Ion Exchange Resin OH (BIO RAD® AG1-X8) was added and the mixture was stirred at room temperature overnight. The mixture was filtered and the solids were rinsed with an additional 250 ml. of water. The original mixture was filtered and the rinse were combined and a small amount was titrated with 0.1N HCl to indicate the presence of 0.24 mol hydroxide (0.24 mol N-butyl-N-cyclooctylpyrrolidinium hydroxide) in the solution.

The synthetic procedure described above is depicted below.

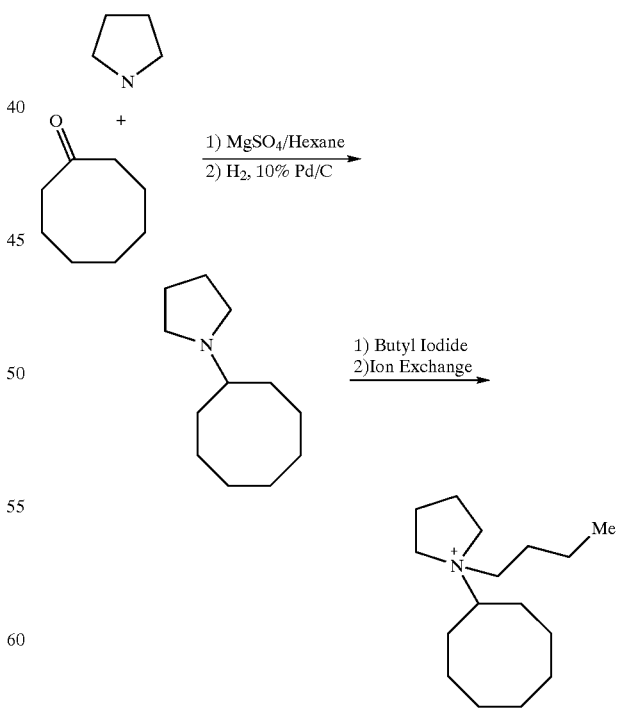

In a manner similar to that of Example 1, N-propyl-cyclooctylpyrrolidinium cation (Template B) can be prepared.

Example 2

Preparation of Borosilicate SSZ-58

A 23 cc. Teflon liner was charged with 6.9 gms. of 0.435M aqueous solution of N-butyl-N-cyclooctylpyrrolidinium hydroxide (3 mmol, Template A), 1.2 gms. of 1M aqueous solution of NaOH (1.2 mmol NaOH) and 3.9 gms. of deionized water. To the resulting mixture, 0.06 gm. of sodium borate decahydrate (0.157 mmol of sodium borate decahydrate, about 0.315 mmol $B_2O_3$) was added and stirred until completely dissolved. Then 0.9 gm. of Cabosil-M-5 fumed $SiO_2$ (about 14.7 mmol $SiO_2$) was added to the solution and the mixture was thoroughly stirred. The resulting gel was capped off and placed in a Parr bomb steel reactor and heated in an oven at 160° C. while rotating at 43 rpm. The reaction was monitored by checking the gel's pH, and by looking for crystal formation using Scanning Electron Microscopy (SEM) at six day intervals. The reaction was completed after heating for 12 days at the conditions described above. Once the crystallization was complete, the starting reaction gel turned to a mixture comprising a clear liquid layer with solids (powder) that settled to the bottom. The mixture was filtered through a fritted glass funnel. The collected solids were thoroughly washed with water and then rinsed with acetone (10 ml.) to remove any organic residues. The solids were allowed to air-dry overnight and then they were oven-dried at 120° C. for one hour. The reaction afforded 0.78 gm. of a very fine powder. SEM showed the presence of only one crystalline phase. The X-ray analysis of the powder indicated that the material was SSZ-58.

Examples 3–16

Synthesis of Borosilicate SSZ-58

The synthesis of Example 1 was repeated keeping the amount of NaOH, water and Cab-OSil M5 the same while varying the amount of $Na_2B_4O_7 \cdot 10H_2O$. The $SiO_2/OH$ mole ratio was 3.5, the $H_2O/SiO_2$ mole ratio was 45 and the $SiO_2/B_2O_3$ and $SiO_2/Na$ mole ratios were as indicated in the table below. The reactions were carried out at 160° C. and 43 rpm.

| Example No. | $SiO_2/B_2O_3$ | $SiO_2/Na$ | Days | Products |
|---|---|---|---|---|
| 3 | 280 | 11.74 | 12 | SSZ-58 |
| 4 | 140 | 11.26 | 12 | SSZ-58 |
| 5 | 93.6 | 10.83 | 12 | SSZ-58 |
| 6 | 70 | 10.42 | 12 | SSZ-58 |
| 7 | 56 | 10.05 | 12 | SSZ-58 |
| 8 | 46.3 | 9.7 | 12 | SSZ-58 |
| 9 | 40 | 9.38 | 12 | SSZ-58 |
| 10 | 35 | 9.07 | 12 | SSZ-58 |
| 11 | 31 | 8.8 | 18 | SSZ-58 |
| 12 | 28 | 8.52 | 18 | SSZ-58 + layered mat'l |
| 13 | 25.5 | 8.27 | 18 | SSZ-58 + layered mat'l |
| 14 | 23.3 | 8.03 | 18 | SSZ-58 (major) + layered mat'l (minor) |
| 15 | 21.55 | 7.81 | 18 | SSZ-58 (major) + layered mat'l (minor) |
| 16 | 18.67 | 7.4 | 21 | SSZ-58 + layered mat'l (minor) |

Example 17

Synthesis of Aluminosilicate SSZ-58

A 23 cc. Teflon liner was charged with 5.2 gms. of 0.435M aqueous solution of N-butyl-N-cyclooctylpyrrolidinium hydroxide (2.25 mmol Template A), 1.5 gms. of 1M NaOH aqueous solution (1.5 mmol NaOH) and 0.75 gm. of deionized water. To the resulting solution, 0.25 gm. of sodium-Y zeolite (Union Carbide LZ-Y52: $SiO_2/Al_2O_3=5$) and 0.80 gm. of Cabosil M-5 fumed $SiO_2$ (about 13 mmol $SiO_2$) was added, consecutively. The resulting mixture was thoroughly stirred and the resulting gel was capped off and placed in a Parr bomb steel reactor and heated in an oven at 160° C. while rotating at 43 rpm. The reaction was monitored by checking the gel's pH, and by looking for crystal formation using SEM at six day intervals. The reaction was completed after heating at the conditions described above for six days. The completed reaction mixture appeared as a colorless liquid with fine white solid settled to the bottom of the Teflon liner. The mixture was filtered through a fritted glass funnel, and the obtained white solids were washed generously with water and then rinsed with a small amount of acetone and allowed to air-dry overnight. The solids were further dried in an oven at 120° C. for one hour. The reaction yielded 0.81 gm. of SSZ-58.

Examples 18–32

Synthesis of Aluminosilicate SSZ-58

The synthesis of Example 17 was repeated using LZ-Y52 as the aluminum source and Cab-O-Sil M5 as the $SiO_2$ source. The $SiO_2/OH$ mole ratio was 8.7, the $H_2O/SiO_2$ mole ratio was 28 and the $SiO_2/Al_2O_3$ and $SiO_2/Na$ mole ratios were as indicated in the table below. The reactions were carried out at 160° C. and 43 rpm.

| Example No. | $SiO_2/Al_2O_3$ | $SiO_2/Na$ | Products |
|---|---|---|---|
| 18 | 317 | 8.4 | SSZ-58 + Trace LZ-Y52 |
| 19 | 158.5 | 8.1 | SSZ-58 + Trace LZ-Y52 |
| 20 | 107.5 | 7.78 | SSZ-58 + Trace LZ-Y52 |
| 21 | 82.5 | 7.5 | SSZ-58 |
| 22 | 66.9 | 7.3 | SSZ-58 |
| 23 | 56.5 | 7.1 | SSZ-58 |
| 24 | 49 | 6.9 | SSZ-58 |
| 25 | 43.5 | 6.7 | SSZ-58 |
| 26 | 39 | 6.6 | SSZ-58 + trace LZ-Y52 |
| 27 | 35.8 | 6.4 | SSZ-58 + trace LZ-Y52 |
| 28 | 33 | 6.26 | SSZ-58 (mostly) + LZ-Y52 |
| 29 | 30.8 | 6.16 | SSZ-58 (mostly) + LZ-Y52 |
| 30 | 26.3 | 5.85 | SSZ-58 (major) LZ-Y52 (minor) |
| 31 | 23.8 | 5.66 | SSZ-58 (major) LZ-Y52 (minor) |
| 32 | 20 | 5.32 | SSZ-58 (major) LZ-Y52 (minor) |

Example 33

Synthesis of All-Silica SSZ-58

A 23 cc. Teflon liner was charged with 6.9 gms. of 0.435M aqueous solution of N-butyl-N-cyclooctylpyrrolidinium hydroxide (3 mmol Template A), 1.2 gms. of 1M NaOH aqueous solution (1.2 mmol NaOH) and 3.9 gm. of deionized water. To the resulting solution, 0.9 gm. of Cabosil M-5 fumed SiO2 (about 14.7 mmol $SiO_2$) was added and the mixture was thoroughly stirred. The resulting mixture was thoroughly stirred and the resulting gel was capped off and placed in a Parr bomb steel reactor and heated in an oven at 160° C. while rotating at 43 rpm. The reaction was monitored by checking the gel's pH, and by looking for crystal formation using SEM at six day intervals. The reaction was completed after heating at the conditions described above for 18 days. The completed reaction mixture appeared as a colorless liquid with solids (powder) settled to the bottom of the Teflon liner. The mixture was filtered through a fritted glass funnel. The collected solids were thoroughly washed with water and then rinsed with acetone (10 ml.) to remove any organic residues. The solids were allowed to air-dry overnight and then dried in an oven at 120° C. for one hour. The reaction yielded 0.73 gm. of pure SSZ-58

Example 34

Seeded Synthesis of Borosilicate SSZ-58

A 23 cc Teflon liner is charged with 6.9 gm of 0.435M aqueous solution of N-butyl-N-cyclooctylpyrrolidinium hydroxide (3 mmol template), 1.2 gm of 1M aqueous solution of NaOH (1.2 mmol NaOH) and 3.9 gm of de-ionized water. To this mixture, 0.06 gm of sodium borate decahydrate (0.157 mmol of $Na_2B_4O_7 \cdot 10H_2O$; ~0.315 mmol $B_2O_3$) is added and stirred until completely dissolved. Then, 0.9 gm of CABOSIL-M-5 (~14.7 mmol $SiO_2$) and 0.04 gm of SSZ-58 (the product of Example 1) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM). The reaction is completed after heating for 5 days at the conditions described above. Once the crystallization is complete, the starting reaction gel turns to a mixture comprising of a clear liquid layer with solids (powder) that settled to the bottom. The mixture is filtered through a fitted-glass funnel. The collected solids are thoroughly washed with water and, then, rinsed with acetone (10 ml) to remove any organic residues. The solids are allowed to air-dry over night and, then, dried in an oven at 120° C. for one hour. The reaction affords 0.85 gram of a very fine powder. SEM shows the presence of only one crystalline phase. The X-ray pattern of the powder is identical to the XRD pattern of the product of Example 1.

Example 35

Calcination of SSZ-58

The material from Example 2 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours, after which it is increased to 594° C. and held there for another 5 hours. A 50/50 mixture of air and nitrogen is passed over the zeolite at a rate of 20 standard cubic feet per minute during heating. The product had the X-ray diffraction data Table IIA above.

Example 36

$NH_4$ Exchange

Ion exchange of calcined SSZ-58 material (prepared in Example 35) is performed using $NH_4NO_3$ to convert the zeolite from its $Na^+$ form to the $NH^+$ form, and, ultimately, the $H^+$ form. Typically, the same mass of $NH_4NO_3$ as zeolite is slurried in water at a ratio of 25–50:1 water to zeolite. The exchange solution is heated at 95° C. for 2 hours and then filtered. This procedure can be repeated up to three times. Following the final exchange, the zeolite is washed several times with water and dried. This $NH_4^+$ form of SSZ-58 can then be converted to the $H^+$ form by calcination (as described in Example 35) to 540° C.

Example 37

Constraint Index Determination

The hydrogen form of the zeolite of Example 17 (after treatment according to Examples 34 and 35) is pelletized at 2–3 KPSI, crushed and meshed to 20–40, and then>0.50 gram is calcined at about 540° C. in air for four hours and cooled in a desiccator. 0.50 Gram is packed into a ⅜ inch stainless steel tube with aluminum on both sides of the zeolite bed. A Lindburg furnace is used to heat the reactor tube. Helium is introduced into the reactor tube at 10 cc/min. and at atmospheric pressure. The reactor is heated to about 315° C., and a 50/50 (w/w) feed of n-hexane and 3-methylpentane is introduced into the reactor at a rate of 8 μl/min. Feed delivery is made via an ISCO pump. Direct sampling into a gas chromatograph begins after 10 minutes of feed introduction. The Constraint Index value is calculated from the gas chromatographic data using methods known in the art, and is found to be 0.57. At 315° C. and 10 minutes on-stream, feed conversion was 37%.

It can be seen that SSZ-58 has very high cracking activity, indicative of strongly acidic sites. The low value of the Constraint Index and the fouling rate of SSZ-58 are typical of a large pore zeolite. In addition, the low fouling rate indicates that this catalyst has a good stability.

Example 38 n-Hexadecane Cracking

The product of Example 17 is treated as in Examples 34 and 35. Then a sample is slurried in water and the pH of the slurry adjusted to a pH of ~10 with dilute ammonium hydroxide. To the slurry is added a solution of $Pd(NH_3)_4(NO_3)_2$ at a concentration which would provide 0.5 wt. % Pd with respect to the dry weight of the zeolite sample. This slurry is left to stand at room temperature for 72 hours. Then, the slurry is filtered through a fritted glass funnel, washed with de-ionized water, and dried at 120° C. for two hours. The catalyst is then calcined slowly up to 482° C. in air and held there for three hours.

The calcined catalyst is pelletized in a Carver Press and crushed to yield particles with a 20/40 mesh size range. 0.5 gm of the catalyst is packed into a ¼" OD tubing reactor in a micro unit for n-hexadecane hydroconversion. Table III gives the run conditions and the products data for the hydrocracking test on n-hexadecane. After the catalyst is tested with n-hexadecane, it is titrated using a solution of butyl amine in hexane. The temperature is increased and the conversion and product data evaluated again under titrated conditions. The results shown in Table III show that SSZ-58 is an effective hydrocracking catalyst.

TABLE III

| | 534° F. | 582° F. |
|---|---|---|
| Temperature | | |
| Time-on-Stream (hrs.) | 33.8–45.7 | 57.7-70.2 |
| WHSV | 1.55 | 1.55 |
| PSIG | 1200 | 1200 |
| Titrated? | No | Yes |
| n-16, % Conversion | 97.7 | 99.4 |
| Hydrocracking Conversion, % | 70.1 | 79.6 |
| Isomerization Selectivity, % | 29.4 | 24.4 |
| Crack. Selectivity, % | 70.6 | 78.1 |
| $C_4$, % | 8.4 | 8.6 |
| $C_5/C_4$ | 7.4 | 7.9 |
| $C_5+C_6/C_5$, % | 25.8 | 28.3 |
| DMB/MP | 0.04 | 0.04 |
| $C_4$–$C_{13}$ I/N | 1.64 | 2.1 |

Example 39

Nitrogen Adsorption

The product of Example 2 is treated as in Examples 34 and 35. Then it is subjected to a surface area and micropore volume analysis using $N_2$ as adsorbate and via the BET method. The BET area is 326 $m^2$/gm. The external surface area of the zeolite is 88 $m^2$/gm and the micropore volume is 0.11 cc/gm.

Example 40

Using a procedure similar to that of Example 2, SSZ-58 is prepared using a N-propyl-cyclooctylpyrrolidinium cation (Template B) as the templating agent.

What is claimed is:

1. In a process for the reduction of oxides of nitrogen contained in a gas stream in the presence of oxygen wherein said process comprises contacting the gas stream with a zeolite, the improvement comprising using as the zeolite a zeolite having a mole ratio greater than about 20 of an oxide of a first tetravalent element to an oxide of a second tetravalent element which is different from said first tetravalent element, trivalent element, pentavalent element or mixture thereof and having, after calcination, the X-ray diffraction lines of Table II.

2. The process of claim 1 wherein said zeolite contains a metal or metal ions capable of catalyzing the reduction of the oxides of nitrogen.

3. The process of claim 2 wherein the metal is copper, cobalt or mixtures thereof.

4. The process of claim 2 wherein the gas stream is the exhaust stream of an internal combustion engine.

* * * * *